United States Patent [19]
Fang et al.

[11] 3,932,134
[45] Jan. 13, 1976

[54] TIME-TEMPERATURE INTEGRATING INDICATOR DEVICE

[75] Inventors: Shou-Mean Fang, Lake Hiawatha; Craig R. Hof, Boonton, both of N.J.

[73] Assignee: Bio-Medical Sciences, Inc., Fairfield, N.J.

[22] Filed: Oct. 16, 1974

[21] Appl. No.: 515,165

[52] U.S. Cl............. 23/253 TP; 23/254 R; 73/356; 73/358; 116/114.5
[51] Int. Cl.².................. G01N 21/06; G01N 21/20; G01N 11/12
[58] Field of Search ........ 23/253 TP, 232 R, 254 R; 426/88; 195/127, 103.5; 116/114.5, 114; 73/339, 356, 358

[56] References Cited
UNITED STATES PATENTS

| | | | |
|---|---|---|---|
| 2,552,477 | 5/1951 | Cole | 73/339 R |
| 2,671,028 | 3/1954 | Clark | 116/114.5 |
| 3,414,415 | 12/1968 | Broad, Jr. | 116/114.5 |
| 3,697,227 | 10/1972 | Goldstein et al. | 23/254 R |

*Primary Examiner*—R. E. Serwin
*Attorney, Agent, or Firm*—Anthony Lagani, Jr.

[57] ABSTRACT

Temperature time integrating indicator device in which a gas generating material located at one end of the device and activated at time of use of the device is absorbed by an indicating wick extending in the device in a direction away from the gas source, which wick changes color to denote a time-temperature integral and hence the temperature history of a product, there being a gas barrier means extending along the longitudinal sides of the wick for inhibiting gas transport to insure that substantially all gas absorbed by the wick makes first contact with the wick at the end nearest the gas source thus precluding first gas contact with the wick at more remote location with consequent erroneous temperature history indication.

7 Claims, 5 Drawing Figures

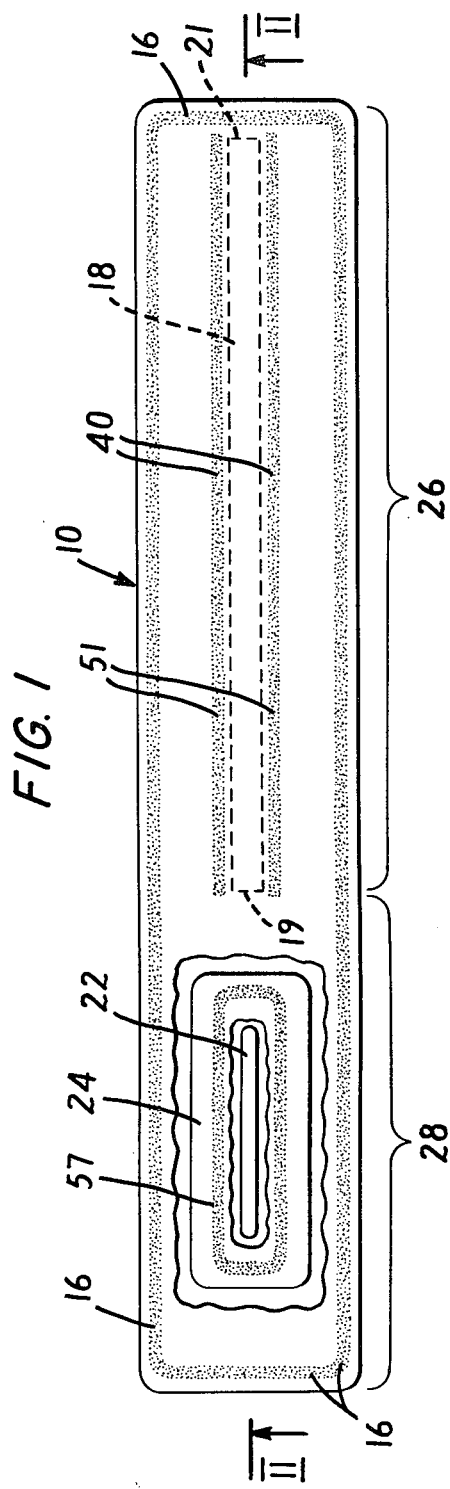
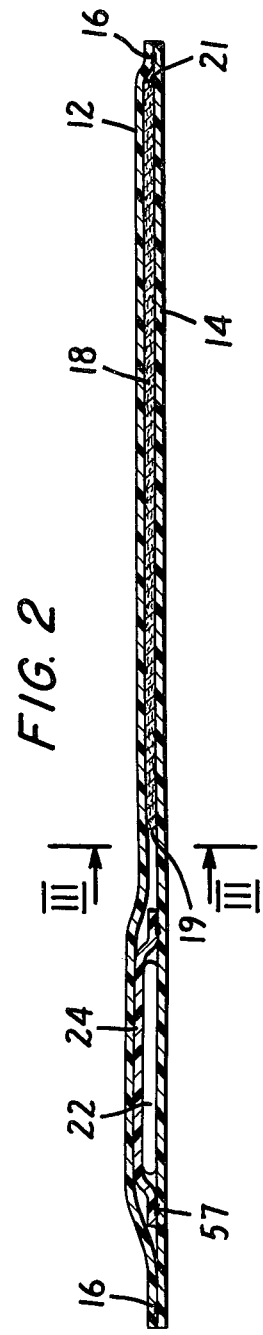
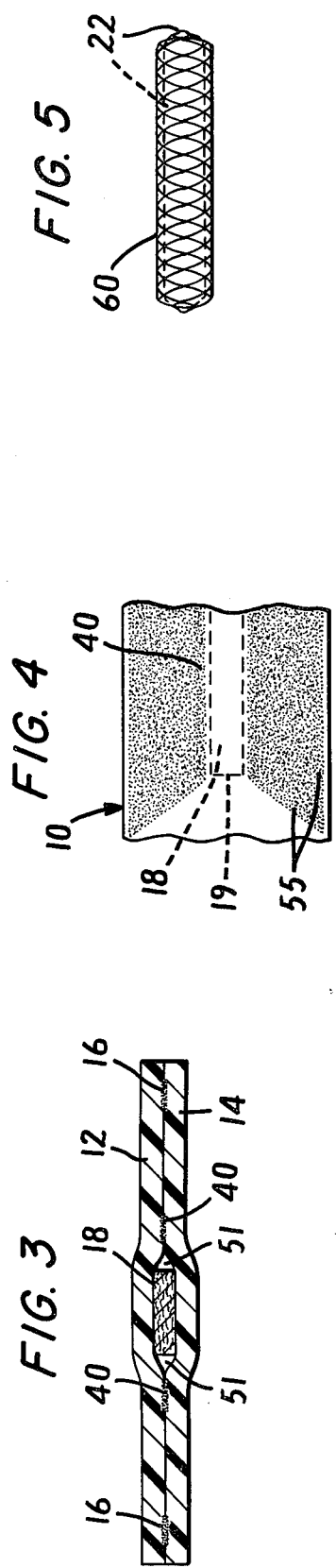

TIME-TEMPERATURE INTEGRATING INDICATOR DEVICE

BACKGROUND OF THE INVENTION

Pending U.S. application Ser. No. 469,851, filed on May 14, 1974 discloses a time-temperature integrating indicator. The device disclosed in said application includes an elongated envelope of upper and lower walls of gas impermeable material which are heat sealed together in a continuous course extending about the periphery of each, with the walls further having a transverse cross-seal intermediate the ends of the envelope so as to define first and second compartments in the envelope. A gas generating material is disposed in the first compartment and wick means extends from the first compartment to the second compartment and intervenes the cross-seal whereby the wick means is the only gas communication between the first and second compartments. Further an indicator composition is deposited on the wick with the indicator composition producing a color change in the presence of gas generated by the gas generating material. The function of such device is to provide a temperature history, e.g., of a product associated with the device in visual display as a color front on the indicator wick with the distance of the front advancement being a function of the temperature time interval, the visual display serving to inform a user whether or not the product has been unduly subjected to adverse temperature conditions as might affect the ultimate product usage. The device is particularly suited for providing indication of the condition of foods, films, pharmaceuticals, biological preparations and the like to give indication of any decomposition, deterioration or change in the sterile character of such products.

While the device disclosed in said pending application functions well and accurately in many monitoring applications, there are certain utilizations wherein the device does not provide optimum results because the cross seal is not effective in all situations to prevent gas communication from the first compartment to the second compartment except through the wick means. As a practical consideration, it is not possible to effect a cross-seal of the envelope that does not leave small passages at either side of the wick. Thus gas transport from the first to the second compartment can occur without the gas contacting the wick in the region of the cross-seal. If there exists free passage space in the second compartment of any significant lateral expanse, as for example as depicted in FIG. 1 of said patent application, random gas molecules may transport through the second compartment to a location well beyond the cross-seal before first contacting the wick means. Also, the previous design is not effective in preventing gas escaping from the wick before reacting, reentering the wick at some location leading the indicator front, and reacting on the wick at this location. In either event, the indicator in the wick will change color at such location possibly giving an erroneous indication, since the indication front should advance progressively along the wick in a direction away from the cross-seal as a direct function of the time-temperature integral to which the device has been subjected. In other words, absorption of gas by the wick and reaction on it desirably should be confined to occurring progressively from the wick end nearest the gas source.

SUMMARY OF THE PRESENT INVENTION

The present invention relates to an improved time-temperature integrating indicator device of the type described in pending application Ser. No. 469,851, the disclosure of which is incorporated herein by reference.

The device of said patent application includes an elongated envelope having generally co-extensive upper and lower walls each of a gas impermeable material with the walls being sealed together in a continuous course extending about the periphery of each, and the walls further being sealed together at a position intermediate their ends by a transverse cross-seal so as to define first and second compartments within the envelope. A gas generating material is disposed in the first compartment and a wick extends from the first compartment to the second compartment and intervenes the cross-seal whereby the wick is intended to provide the only gas communication between the two compartments. Finally, an indicator composition producing a color change in the presence of a gas generated by the gas generating material. When it is desired to employ the device, the gas generating material, which normally is confined in a further enclosure within the device first compartment, is activated by rupturing the enclosure causing the gas generating material to produce a gas which is communicated from the first to second compartments through the cross-seal and onto the wick. According to the time and temperature exposure of the product with which the device is used, the said exposure as an integral of time and temperature will be recorded in the device on the wick.

In accordance with the present invention spurious, random gas molecules transport within a time-temperataure integrating indicator device of the type disclosed in said application is eliminated as a factor in the operation of the device by providing a longitudinally disposed gas barrier means extending between the indicator envelopes upper and lower walls immediately adjacent each longitudinal side margin of the wick and along substantially the full length of the wick. If any gas should bypass the end of the wick nearest the gas source, the spaces between the barrier and the wick side margin is sufficiently small to insure that the gas will not travel longitudinally of the wick to any appreciable or significant distance before it is caused to come into contact with the wick. Thus substantially all gas absorbed by the wick is caused to make first contact with the wick at or right adjacent to the end of the wick closest to the gas source.

Desirably the gas barrier means is provided by sealing the upper and lower walls of the envelopes together in a course along each side of the wick longitudinal margins. Most conveniently, and where the envelope walls are heat sealable materials, the barrier is achieved by effecting a heat sealed joinder of the walls.

The present invention also provides an improved manner of confining the gas generating material in the device, the said material being confined in a readily rupturable or frangible ampule. Conveniently the ampule can be provided as an elongated glass cylinder with the glass cylinder being sealed at the opposite ends thereof, the gas generating material being activated when the glass cylinder is ruptured. Additionally, the ampule is fixedly positioned in the envelope by an overlaying strip of gas permeable material which is fixedly secured to the inner surface of one of said upper and lower walls by means of a heat seal encircling the ampule. Further, the ampule can be enclosed in a resilient sleeve so that when it is ruptured, particles of the broken glass are prevented from damaging the envelope as by piercing the same when the ampule is ruptured.

The invention accordingly comprises the temperature-time integrating indicator device possessing the features, properties and relation of elements which will be exemplified in the device hereinafter described and the scope of the invention will be indicated in the claims.

BRIEF DESCRIPTION OF THE DRAWINGS

Other objects of the invention will be in part obvious and will in part appear from the following detailed description taken in conjunction with the accompanying drawings, wherein like reference numerals indicate like parts throughout and which FIG. 1 is a plan view of a temperature-time integrating indicator device constructed in accordance with the principles of the present invention, portions of the upper wall and the ampule positioning strip being broken away for purposes of clarity in depicting constructional details.

FIG. 2 is a longitudinal vertical sectional view as taken along the line II—II in FIG. 1.

FIG. 3 is a transverse sectional view on enlarged scale as taken along the line III—III in FIG. 2.

FIG. 4 is a fragmentary plan view of the device showing an additional manner in which the sealing together of the envelope walls can be carried out.

FIG. 5 is a side view of the ampule in which the gas generating material is confined, the ampule being enclosed in a resilient sleeve.

DESCRIPTION OF THE PREFERRED EMBODIMENT

In the ensuing descriptinon reference is made to gas permeable and gas impermeable materials as well as to gas generating materials, wick means, and indicator compositions. Various types of materials can be employed for such components as is described in more elaborate detail in said pending applicaton Ser. No. 469,851 and for which purpose the disclosure of said application is incorporated herein by reference. Further description herein is intended to include for such components, the materials disclosed in said application as well as such other materials as would be apparent to those skilled in the art.

With continuing reference to FIGS. 1–3, there is depicted a temperature time indicator which includes an envelope 10 comprised of elongated, generally coextensive upper and lower walls 12 and 14 of gas impermeable material. The walls 12 and 14 while depicted as single ply components of transparent material could be plural ply and be laminated to include a metal foil layer as well as being in part opaque. The important consideration is that said walls be gas impermeable. Walls 12 and 14 are joined together to form the envelope structure by sealing them together in a continuous course extending about the periphery of each, e.g., by heat-sealing, the material of the walls of course being compatible to that purpose, and such peripheral seal being shown generally at 16 in FIG. 2. The device also embodies a wick 18, the wick being disposed longitudinally of the envelope 10, in a longitudinal portion thereof which constitutes an indicating section 26, and being treated with an indicator composition as described in said earlier-mentioned pending patent application. The device also includes an ampule 22 disposed in another longitudinal portion of the envelope constituting a gas generation section 28 in which is confined a gas generating material, the ampule being disposed intermediate the upper and lower walls 12 and 14 and being fixedly positioned there-between as by connection of an overlaying gas permeable sheet 24 with one of said walls, the wick 18 having one tip end as at 19 in gas generation section 26 and its other tip end 21 remote from said gas generation section.

In accordance with the present invention, there is provided a gas barrier 40 at each longitudinal side of the wick 18, the gas barrier extending between walls 12 and 14 and in the instance where walls 12 and 14 are amenable to heat sealing being provided by effecting a heat sealed joinder of the walls in the pattern depicted best in FIG. 1. The heat seal is positioned immediately adjacent the said wick longitudinal side margins. "Immediately adjacent" as used herein is intended to mean effecting the heat seal as close to the wick as practical manufacturing will permit without causing adherance of any melted wall material to the wick material. Thus any spacing 51 as may exist between the sides of the wick at the barrier is of insignificant consequence with respect to the possibility of gas transport occurring along said space without making a contact with the wick 18 at or very close to tip end 19. In this manner the possibility of random gas molecules transport through said space and into first contact with the wick at location remote from tip end 19 is inhibited.

The important requirement in the construction of the device is that the longitudinal gas barrier extend immediately adjacent the wick side margins substantially along the full length of the wick. If desired, however, the sealed joinder of the envelope walls can be extended laterally outwardly from the wick sides in the pattern 55 depicted in FIG. 4.

Further in accordance with the present invention, the gas generating component is confined within ampule 22, and the ampule 22 is fixedly secured to the inner surface of one of the envelope upper and lower walls, in the depicted embodiment the ampule 22 being fixedly positioned by securing the same to the inner surface of lower wall 14 with the gas permeable sheet 24, the latter being heat sealed to the lower wall in the generally oval course seal pattern 57 depicted in FIG. 1. The ampule 22 in which the gas generating material is confined desirably is an elongated component, closed at its ends and made of a frangible material, glass being preferred. Thus, when it is desired to activate the device, the user need only apply a bending force to the envelope in the region of the position of the ampule and generally applied intermediate the ends of the ampule to fracture the same and permit the gas to escape in the first section 26 of the envelope from whence it can flow onto the wick located in the second section 28. To provide that when ampule 22 is ruptured, resulting jagged particles of the same will not pierce or damage any of the envelope structure, the ampule can be enclosed in a resilient sleeve 60 as shown in FIG. 5, the resilient sleeve for example being a braided fiberglass member.

The improved device of the present invention is used in the same manner as the device described in the earlier-mentioned pending application, being used in association with a product that is received in a particular environment wherein the temperature history is to be measured in order to determine how if at all departure from a desired norm as might affect the product. At the time the product is placed in the environment and it is desired to provide a history of the storage of the product, the device is activated by breaking the glass ampule and the operation of the device thereafter proceeds as is set forth in said pending application.

In summary, this application discloses an improvement in design of the time temperature intergrating indicator of pending U.S. application Ser. No. 469,851, whose purpose is twofold. First, to insure that no significant amount of gas leaves the first compartment and enters the second compartment other than through the wick means. Second, to prevent any significant amount of gas leaving the wick and reentering and reacting at a location as to give erroneous indication.

What is claimed is:

1. A temperature time integrating indicator device which comprises an elongated envelope having generally co-extensive upper and lower walls each of a gas impermeable material, the walls being sealed together in a continuous course extending about the periphery of each, a first longitudinal portion of said envelope comprising a gas generation section within said envelope and a second longitudinal portion of said envelope comprising an indicating section within said envelope, a gas generating material disposed in the gas generation section of said envelope, an elongated wick disposed longitudinally of the envelope with one end thereof in said gas generation section, said wick extending a distance along said envelope indicating section and the other end thereof being remote from said gas generation section, an indicator composition deposited on said wick, said indicator composition producing a color change in the presence of gas generated by said gas generating material, and longitudinally disposed gas barrier means extending between said upper and lower walls immediately adjacent each longitudinal side margin of said wick and along substantially the full length of said wick for inhibiting gas transport at the longitudinal side margins of said wick whereby substantially all gas absorbed by said wick makes first contact with said wick at said one end thereof.

2. The device of claim 1 in which said gas barrier means comprises a sealed together connection of said upper and lower walls.

3. The device of claim 2 in which said upper and lower walls are each of material amenable to heat sealing, said gas barrier means comprising a heat-sealed joinder of said upper and lower walls.

4. The device of claim 1 in which said gas generating material is confined in an ampule of readily rupturable material, said ampule being fixedly disposed in the gas generation section of said envelope.

5. The device of claim 4 in which said ampule is a glass cylinder.

6. The device of claim 4 in which said ampule is enclosed in a resilient sleeve for preventing damaging the envelope structure when said ampule is ruptured.

7. The device of claim 4 in which said ampule is fixedly positioned in said first compartment by a strip of gas permeable material sealed to an inner surface by one of said upper and lower walls in a course encircling said ampule.

* * * * *